United States Patent [19]

Bruce

[11] Patent Number: 5,416,878
[45] Date of Patent: May 16, 1995

[54] SURGICAL METHODS AND APPARATUS USING A BENT-TIP SIDE-FIRING LASER FIBER

[75] Inventor: Johnny M. Bruce, Spring, Tex.

[73] Assignee: Endeavor Surgical Products, Inc., The Woodlands, Tex.

[21] Appl. No.: 193,431

[22] Filed: Feb. 8, 1994

Related U.S. Application Data

[63] Continuation-in-part of Ser. No. 99,203, Jul. 29, 1993, abandoned.

[51] Int. Cl.$^6$ .................. G02B 6/02; A61B 19/00; A61B 17/32
[52] U.S. Cl. ................................ 385/123; 385/116; 385/117; 385/147; 128/4; 128/6; 128/897; 128/898; 606/15; 606/16; 606/17
[58] Field of Search ............... 385/31, 32, 38, 47, 385/100, 115, 117, 123, 147, 901, 902; 128/4, 6, 7, 303.1, 897, 898, 899; 606/15, 16, 17; 604/20, 22, 49, 53

[56] References Cited

U.S. PATENT DOCUMENTS

| | | | |
|---|---|---|---|
| 4,517,974 | 5/1985 | Tanner | 128/303.1 |
| 4,538,609 | 9/1985 | Takenaka et al. | 128/303.1 |
| 4,693,244 | 9/1987 | Daikuzoni | 128/303.1 X |
| 4,740,047 | 4/1988 | Abe et al. | 128/6 X |
| 4,804,248 | 2/1989 | Bhagavatuia | 385/43 X |
| 5,031,980 | 7/1991 | Colles et al. | 385/123 X |
| 5,041,109 | 8/1991 | Abela | 606/15 |
| 5,053,033 | 10/1991 | Clarke | 606/3 |
| 5,129,897 | 7/1992 | Daikuzono | 606/16 |
| 5,139,495 | 8/1992 | Daikuzono | 606/17 |
| 5,190,535 | 3/1993 | Daikuzono | 606/13 |
| 5,207,672 | 5/1993 | Roth et al. | 606/10 |
| 5,290,280 | 3/1994 | Daikuzono | 606/16 |
| 5,304,170 | 4/1994 | Green | 606/9 |
| 5,312,399 | 5/1994 | Hakky et al. | 606/15 |
| 5,320,617 | 6/1994 | Leach | 606/15 |
| 5,328,488 | 7/1994 | Daikuzono | 606/16 |

FOREIGN PATENT DOCUMENTS

| | | | |
|---|---|---|---|
| 63-215257 | 3/1990 | Japan | 385/32 X |
| 64-35841 | 8/1990 | Japan | 385/35 X |
| PCT/US92/-11368 | 7/1993 | WIPO | 17/36 |

OTHER PUBLICATIONS

Regulatory Issues Surround Laser BPH Tx, by Michael Moretti, Urology Times, May 1993, pp. 12–14.
Minimally Invasive Therapies of the Prostate, by G. M. Watson MS, FRCS, Minimally Invasive Therapy, 1992, vol. 1, pp. 231–240.
Medical Laser Insight, by Medical Insight, Inc., vol. 1, No. 6, Jun. 1993.

*Primary Examiner*—Brian Healy
*Attorney, Agent, or Firm*—Workman, Nydegger & Seeley

[57] ABSTRACT

An improved side-firing laser fiber assembly is provided in which the output end terminates in a substantially flat face having an arcuate edge around the circumference thereof. The presently preferred fiber has a preferred diameter of about 1000 microns and is made from quartz, silica or a thermoplastic. A bend is preferably located approximately 1.5 millimeters proximally of the emitting face of the fiber, and has a preferred bend angle of about 135 to 145 degrees, resulting in a laser beam directed approximately 30 degrees off-axis of the main body of the optical fiber suitable for use in a non-contact mode to effect deep tissue coagulation and tissue necrosis. The configuration of the optical fiber minimizes burning and cracking typically associated with quartz fibers without the need for a protective metal cap. It operates much cooler than conventional metal-capped fibers, so that it does not generally stick to tissue with which it inadvertently comes into contact during use, and does not usually require irrigation cooling. The foregoing attributes make the apparatus of the present invention particularly useful in treatment of benign prostatis hyperplasia as well as other surgical procedures for which side-firing laser fiber assemblies are useful.

37 Claims, 1 Drawing Sheet

SURGICAL METHODS AND APPARATUS USING A BENT-TIP SIDE-FIRING LASER FIBER

This application is a continuation-in-part of application Ser. No. 08/099,203 filed Jul. 29, 1993, now abandoned, for "Methods and Apparatus For Treating Benign Prostatic Hyperplasia Using a Side-Firing Laser Fiber," which application is incorporated herein by reference in its entirety.

BACKGROUND OF THE INVENTION

1. Technical Field

The present invention relates to optical laser fibers and methods of using them in surgical procedures. More particularly, the present invention relates to side-firing laser fibers and methods of using them in the treatment of various surgical procedures, such as benign prostatic hyperplasia.

2. Background Information

Optical lasers, such as Nd:YAG lasers, have found increasing applications in the conduct of surgical procedures. One advantage of laser surgery is that it can often be performed through a relatively small incision or by insertion into an existing body passageway. Laser surgical procedures can frequently be performed on an outpatient basis, resulting in significantly lower cost and less inconvenience to the patient. Dramatic shortening in recovery time is often seen in comparison to traditional surgery which it replaces. For these reasons, efforts continue to be directed toward the development of new laser apparatus and improved methods of surgical treatment using medical lasers.

Various configurations of optical fibers have been developed for different types of surgical procedures. Recently, side-firing fibers have been found particularly useful in a variety of situations. A typical side-firing laser optical fiber utilizes a mirror or other optical surface to reflect a laser beam traveling down a fiber so as to emerge from the tip of the fiber at a selected angle. This permits the laser beam to be directed onto tissue surrounding body passageways, or the like, without any incision being required. It also permits use of lasers in other cramped environments.

One use for which side-firing fibers is currently being tested is in connection with the treatment of benign prostatic hyperplasia, often referred to as "BPH" for purposes of brevity. BPH is a condition involving an enlarged prostate gland, typically increasing between about two and four times normal size. This condition occurs in approximately one-third of all males over age 60. Currently, approximately 400,000 cases are treated each year in the United States alone, and this number can be expected to increase as the population ages.

BPH is characterized by nocturia (bed-wetting), hesitancy in urination, decreased force of urinary stream, post-voiding dribbling, and a sensation of incomplete emptying. Although incontinence is the most common and emotionally disturbing complaint, it is possible for the enlargement to continue to the point of acute urinary retention. That problem is both painful and dangerous, requiring immediate treatment.

The most common treatment at the present time is known as transurethral resection of the prostate ("TURP"), which involves removal of portions of the prostate gland using a special cytoscope inserted into the urethra. Following a TURP procedure, a typical patient must wait about seven to fourteen days before resuming normal activities, and there is a high incidence of post-operative problems. For example, about 95% of TURP patients experience retrograde ejaculation. It has also been reported that it may take upward of 50 to 100 procedures for an physician to attain true skill at performing TURP procedures; one can only wonder at the fate of the first 50 to 100 patients of each such physician.

Although testing is still far from complete, initial reports indicate that laser treatment of BPH is an improvement over TURP procedures. One such procedure involves the use of side-firing fibers to direct Nd:YAG laser energy onto enlarged prostate tissue. This results in some surface ablation, but the primary benefit is deep tissue coagulation and subsequent tissue necrosis, which effects a reduction in the size of the prostate over a period of several months following the procedure as the necrotic tissue sloughs off. This technique is reported to be much easier to perform, resulting in proficiency after only five to ten procedures. It also has a much lower reported incidence of problems such as retrograde ejaculation—only about 25% of patients report that adverse side-effect.

Hence, it will be appreciated that BPH looms as a major problem for which side-firing laser fibers have shown promise in treating. Yet, side-firing fibers suffer from drawbacks which require improvement.

For example, even though side-firing fibers are intended to be used in a non-contact mode so that laser energy will penetrate into the tissue rather than simply ablate surface tissue, it is not uncommon for the fiber to inadvertently come into contact with the tissue during a laser surgical procedure. It is well known that unprotected quartz fibers become burnt and broken when they come into contact with tissue. To overcome this problem, it has become common to protect quartz fibers with a metal cap which will not break or burn when it inadvertently comes into contact with a patient's tissue. The use of a metal cap causes other problems, however. For example, leakage of laser energy causes metal tips to become heated. When inadvertently touched to tissue, it is common for such heated tips to stick to and thereby cause unwanted damage to tissue. The damage is exacerbated when the tip is forcibly removed from the tissue to which it has become stuck. Although it is usual to irrigate metal tipped fibers in order to try and lower the temperature of the metal tips, such irrigation is frequently only partly successful. Hence, even when using irrigation, some damage occurs due to inadvertent touching of the tip to tissue.

Further, it occasionally happens that a laser is fired accidentally while the tip is outside the patient or when the irrigation is not in operation. When this happens with a side-firing tip using a metal cap, the tip is usually damaged and becomes unusable.

From the foregoing, it will be appreciated that it would be a significant improvement if new side-firing laser fibers were to be developed which would avoid the problems of unprotected quartz tips, yet would also avoid the problems encountered when one uses a metal cap to protect the tip of a quartz fiber. It would also be an important advance if improved methods were to be developed for treatment of BPH or other maladies treatable by side-firing laser fibers.

SUMMARY OF THE INVENTION

It is a primary object of the present invention to provide improved side-firing laser fibers.

It is another object of the present invention to provide a relatively low-cost side-firing fiber that is significantly less likely to cause heat damage to tissue with which it comes in contact than currently available fibers.

Yet another object of the present invention is to provide side-firing fibers which are not easily damaged if fired in open air or if fired while in contact with tissue.

Yet another object of the present invention is to provide improved side-firing fibers which are less likely to become overheated during use than currently available fibers.

A further object of the present invention is to provide improved methods for treating BPH and other surgical procedures suitable for the use of side-firing fibers.

Additional objects and advantages of the invention are set forth hereinbelow in the detailed description, or will be appreciated by the practice of the invention.

To achieve the foregoing objects, and in accordance with the invention as embodied and broadly described herein, the present invention provides an improved side-firing laser fiber assembly in which the output end of an optical fiber terminates in a substantially flat face having an arcuate edge around the circumference thereof. A bend is located substantially adjacent to the end of the fiber, resulting in a deflection of the laser beam so that it is directed approximately off-axis from the main body of the optical fiber. Such a deflection makes the fiber suitable for use in a side-firing non-contact mode capable of effecting deep coagulation and tissue necrosis. The presently preferred fiber has a diameter of about 1000 microns and is made from quartz, silica or a thermoplastic.

Surprisingly, the bent tip configuration of the present invention has been found to avoid the burning and cracking typically associated with quartz fibers, and does so without the need for a protective metal cap. The apparatus of the present invention has been found to operate much cooler than conventional metal-capped fibers, so that it will not generally stick to tissue with which it inadvertently comes into contact during use, and does not usually require cooling by means of irrigation.

The attributes of the apparatus of the present invention benign prostatis hyperplasia, wherein deep coagulation and subsequent tissue necrosis is effective in bringing about a cure or diminishment of symptoms. However, it is also useful in other procedures where side-firing laser fibers are appropriate.

BRIEF DESCRIPTION OF THE DRAWING

In the accompanying drawing, which represents the best mode presently contemplated for carrying out the present invention.

DETAILED DESCRIPTION OF THE PREFERRED EMBODIMENT

Figure 1:
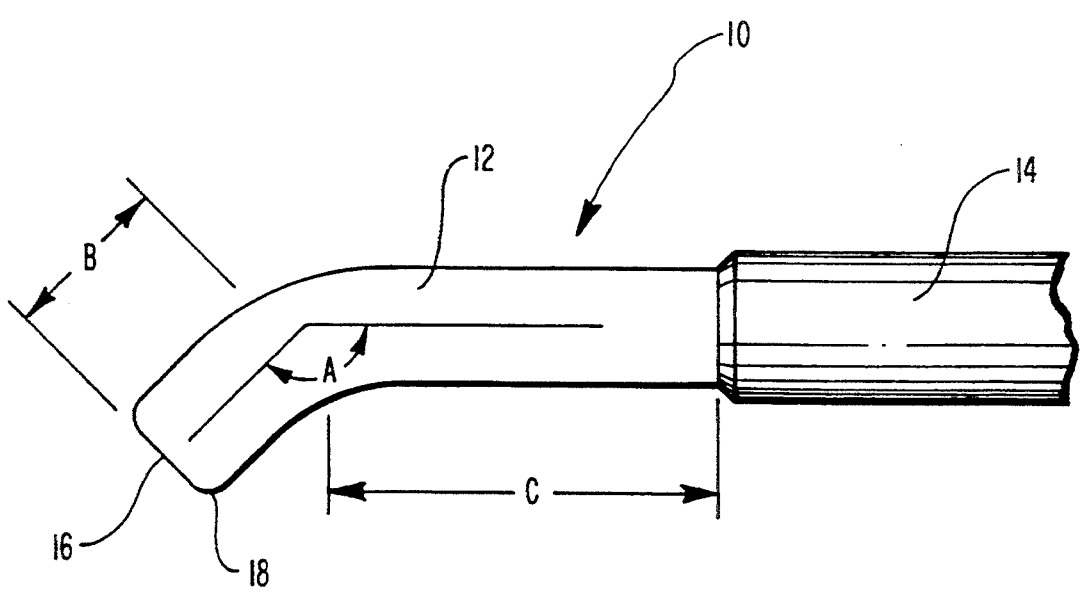
FIG. 1 is a side elevation of the emitting end of a preferred embodiment of a side-firing laser optical fiber in accordance with the present invention used to perform laser surgery.

The present invention is directed to a novel side-firing laser fiber and associated methods for conducting laser surgery. The methods and apparatus of the present invention are particularly useful in the practice of benign prostatic hyperplasia (BPH) and other procedures involving non-contact treatment by a laser beam in order to effect deep coagulation and subsequent necrosis of tissue.

FIG. 1 illustrates the emitting or output end of one presently preferred fiber assembly 10 prepared in accordance with the present invention. Preferably, fiber assembly 10 includes an optical fiber 12 which serves as an optical waveguide for delivering laser energy from a medical laser (not shown). Optical fiber 12 is advantageously protected by a reinforcing jacket member 14.

Fiber 12 may be constructed of various materials, but is preferably formed from quartz, silica, or a thermoplastic such as polycarbonate. For typical applications, it is preferred that fiber 12 have a diameter of about 1000 microns, although fibers having other diameters (larger or smaller) may also be useful for particular applications.

Jacket member 14 may be of a conventional construction. A common form of jacket member 14 would include a cladding material surrounding optical fiber 12, and a teflon or nylon coating over the cladding. Jacket member 14 provides mechanical support for fiber 12 so that the fiber will not break during ordinary use, and also protects most of the length of the optical fiber from scratches or other damage which would result in leakage of laser energy. Additionally, the difference in refractive index between fiber 12 and jacket member 14 efficiently directs the laser energy through the fiber waveguide rather than leaking therefrom.

The input end (not shown) of fiber assembly 10 is typically fitted with a connector (not shown) which permits it to be optically coupled to a medical laser which serves as a source of laser energy. Commonly, an industry standard SMA-905 connector is provided on the input of the fiber assembly in well-known fashion in order to permit the optical fiber to be readily connected to many brands of medical lasers.

The output end of the fiber comprises an emitting face 16. Emitting face 16 is preferably flat and polished so as to emit an unfocused beam of laser energy with little backscattering or reflection, thereby causing substantially all of the laser energy from a laser source to be emitted from the emitting face 16. As illustrated, the tip is bent off-axis from the remaining length of fiber at a location proximally of but adjacent to the emitting face so that laser energy will be emitted at a side-firing angle with respect to the longitudinal axis of the main body of the laser fiber.

The laser assembly of the present invention is useful in either an irrigated environment or a non-irrigated environment. Nevertheless, some features of the invention are usually intended to be altered depending whether the fiber assembly will be used in an irrigated or non-irrigated environment. This is because an Nd:YAG laser beam used for laser surgery and a helium/neon laser beam used as an aiming beam are affected to different extents depending upon whether the emitting face of the laser assembly is immersed in air or water. The following discussion has been separated so as to identify the changes which cause the two beams to have a similar aiming point depending upon the environment.

First will be described dimensions and characteristics particularly suitable for use in nonirrigated surgical procedures. In connection with a non-irrigated use, the presently preferred length of measurement B between the emitting face and the bend is in the range of about 0.5 millimeters to about 2.0 millimeters, and is most preferred to be about 1.5 millimeters. It is preferred that bend angle A with respect to the longitudinal axis of the main body of the optical fiber have a value in the range of about 90 degrees to about 160 degrees, and it is most preferred that bend angle A have a value of about 135 degrees. Values of angle A and measurement B in these ranges are particularly suitable for use with a Nd:YAG laser and a helium/neon laser aiming beam in non-irrigation situations because such an arrangement has been found to result in a generally common aiming point for both of these beams.

When the distance from the bend to the emitting face of a 1000 micron fiber is about 1.5 millimeters, it has been determined that use of a bend angle A of about 135 degrees will direct an unfocused beam of Nd:YAG laser energy in a non-irrigated environment at an angle of about 30 degrees off-axis of the main length of the optical fiber. This has been found to be a useful angle for directing laser energy toward tissue to the side of optical fiber assembly 10, permitting it to function as a side-firing laser fiber. A greater value of bend angle A results in less bend of the beam of laser energy. Although useful in some situations, this is generally less preferable because it tends to lengthen the distance between the end of the fiber and the area to be irradiated. Decreasing the value of bend angle A below 135 degrees may unacceptably shorten the distance between the emitting face and the area of irradiation for some applications, and may also result in some losses due to leakage or backscattering. Nevertheless, it is to be understood that a choice of a bend angle A within the range identified above is contemplated as being useful in connection with the practice of the present invention.

In order to provide support for the exposed portion of optical fiber 12, it is preferred that the jacket member not be stripped too far back. Yet, if the jacket member is too close to the area of the bend, it is subject to heat damage during manufacture of the bend or during use of the fiber to conduct surgery. It has been determined with respect to a 1000 micron fiber, that a distance C between the bend and the end of jacket member 14 is preferred to be in the range of about 2 to 8 millimeters, and it is most preferred that distance C be in the range of about 3.5 to about 5.5 millimeters.

It has been determined that in surgical procedures involving irrigation, use of a fiber assembly 10 as described above may not accurately point to the area where the Nd:YAG laser beam will contact due to differences in indices of refraction. Accordingly, for use in an irrigated environment, it is preferred that some dimensions be altered in order to better direct both the aiming beam and the Nd:YAG beam to nearly the same point on a patient's tissue. For irrigation use, bend angle A is preferably maintained in the range of about 135 degrees to about 155 degrees, with 145 degrees being the most preferred angle. It is preferred that length B be in the range of about 0.5 to about 2.0 millimeters, and most preferably about 1.5 millimeters. Length C is preferably in the range of about 0.5 to about 12.5 millimeters, and most preferably about 3.5 millimeters.

An important feature of the present invention is providing the circumference of the emitting face 16 with an arcuate edge 18 rather than an abrupt 90 degree edge such as has been common in conventional optical fibers. When using a 1000 micron fiber, the presently preferred radius of arcuate edge 18 is in the range of about 0.15 to about 0.30 millimeters, and it is most preferred that the radius be approximately 0.19 millimeters. Utilization of a fiber assembly incorporating an arcuate edge has unexpectedly been found to reduce or prevent damage to tissue, even when the tip contacts tissue being irradiated with laser energy.

This unexpected advantage avoids the need to protect the tip with metal or other material. By avoiding the use of a metal tip in the traditional manner of side-firing fibers, the tip remains much cooler. This reduces or avoids the need to irrigate the surgical site, and even permits the fiber to be fired in air without damage to the tip. Further, it has been discovered that the tip is much less likely to adhere to tissue with which it is inadvertently brought into contact during use, nor is it likely to become burnt or broken.

The optical fiber assembly of the present invention may be easily constructed. For example with respect to manufacture of the non-irrigated embodiment of FIG. 1, the jacket member 14 is stripped back approximately 3 to 6 centimeters from the end of the fiber. If a jacket member using cladding consisting of plastic or a polymer material is involved, any remaining cladding can be removed by means of an electric arc device. If the cladding is glass, it need not be removed. The fiber 12 is then cleaved at a distance approximately 7 to 9 millimeters from the end of the jacket member so as to form a flat emitting face 16 which is perpendicular to the axis of the fiber. Preferably, the flat face is then polished in a conventional manner to remove scratches or other imperfections.

To add the bend angle A, it is presently preferred that a torch be used to heat the fiber until it softens adequately to be bent. This is advantageously accomplished by placing the fiber perpendicular to the flame at the point where the bend is to be placed. Care should be taken to insure that the flame does not come into contact with the fiber jacket. Once the tip of the fiber becomes sufficiently molten, a downward force is applied with a metal probe so as to cause the tip to assume the desired bend angle A. The fiber is then removed from the flame and permitted to cool. A suitable connector may be attached to the input end of the fiber for attachment to a medical laser.

Use of a flame in this manner has been found to cause sufficient heating of the fiber to cause the circumference of the flat face of emitting face 16 to become slightly molten. Without any additional steps being required, this results in the formation of arcuate edge 18. Care must be taken to insure that the flat face does not become so molten as to become rounded, but the proper technique is quickly developed and is easily reproduced in light of the teachings set forth herein.

An optical fiber assembly constructed in accordance with the foregoing is particularly useful as a side-firing fiber for use in effecting deep tissue coagulation and necrosis. A presently preferred use of the fiber assembly of the invention is in the treatment of BPH, although it is also suitable for other procedures involving the use of deep tissue coagulation and necrosis.

In order to treat BPH, a suitable optical fiber assembly is selected, depending upon whether it is to be used in a non-irrigated or an irrigated environment. The optical fiber assembly is preferably used together with a suitable endoscopic instrument. The term "endoscopic instrument" is to be understood broadly, encompassing not only endoscopes, but also cytoscopes and other instruments used for introducing a laser fiber under visual control. The endoscopic instrument is then inserted to the appropriate site for laser surgery with the side-firing laser and the laser is operated so as to effect deep tissue necrosis.

The side-firing laser fiber of the present invention is particularly useful for treatment of BPH. An endoscopic instrument fitted with optical fiber assembly 10 is inserted through the patient's urethra and advanced to the location of the enlarged prostate. To accommodate use with an endoscope or cytoscope small enough to be inserted into a urethra, optical fiber 12 should preferably be 1000 microns in diameter, or less. Taking care to prevent the fiber from touching the surrounding tissue, the laser is activated and the laser beam is directed onto the area of tissue requiring deep coagulation. Although it is anticipated that the surgeon will utilize irrigation in the conventional fashion, the lower temperature of the emitting tip of fiber assembly 10 of the present invention permits dispensing with irrigation. Regardless whether irrigation is used, inadvertent touching of the fiber to tissue rarely results in the fiber becoming stuck to the tissue, and hence avoids or lessens damage which is one of the principal detriments of conventional side-firing fibers in the treatment of BPH.

From the foregoing, it will be appreciated that the present invention provides substantially improved side-firing laser fiber assemblies. As mentioned above, it is well-known that quartz or silica fibers will become burnt and broken during use. This characteristic of fibers made from these materials have caused problems in the past which have been sought to control by the use of metal tips. The present invention offers an improved solution to the problem of burning or breaking quartz or silica fibers in the event they come into contact with tissue during surgical use. Indeed, it is an unexpected and surprising advantage that fibers constructed as discussed in connection with the present invention do not become as heated as do metal capped fibers, thereby reducing damage to tissue if accidentally touched, and also do not easily become burned or broken if they are inadvertently brought into contact with tissue during a surgical procedure. It has also been discovered that side-firing laser fibers in accordance with the present invention do not become easily damaged even if fired outside the patient or when irrigation is not in operation. The foregoing characteristics mark a significant advance in the field of side-firing laser fibers. Such improved fibers can be produced at relatively low cost, and hence are easily disposable after each use.

It will be appreciated that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by U.S. Patent is:

1. A side-firing laser fiber assembly for use in performing laser surgical procedures, comprising:
    an optical fiber, said optical fiber having an input end and an output end,
        the input end being adapted for connection to a laser source, and
        the output end terminating in a substantially flat face from which substantially all of the laser energy from said laser source is emitted,
        said face having an arcuate edge around the circumference thereof,
        said output end having a bend formed proximally of said flat face so that laser energy emitted from said flat face is directed at a side-firing angle with respect to the longitudinal axis of the main body of the optical fiber; and
    a jacket member over most of the length of the optical fiber member.

2. A side-firing laser fiber assembly as defined in claim 1, wherein the bend formed proximally of the flat face is at an angle in the range of approximately 90 to 160 degrees with respect to the longitudinal axis of the main body of said optical fiber.

3. A side-firing laser fiber assembly as defined in claim 1, wherein the bend formed proximally of the flat face is at an angle in the range of approximately 135 to 155 degrees with respect to the longitudinal axis of the main body of said optical fiber.

4. A side-firing laser fiber assembly as defined in claim 1, wherein the bend formed proximally of the flat face is at an angle of approximately 135 degrees with respect to the longitudinal axis of the main body of said optical fiber.

5. A side-firing laser fiber assembly as defined in claim 1, wherein the bend formed proximally of the flat face is at an angle of approximately 145 degrees with respect to the longitudinal axis of the main body of said optical fiber.

6. A side-firing laser fiber assembly as defined in claim 1, wherein the bend is located approximately 0.5 to about 2.0 millimeters from the face of the output end of the optical fiber.

7. A side-firing laser fiber assembly as defined in claim 1, wherein the bend is located approximately 1.5 millimeters from the face of the output end of the optical fiber.

8. A side-firing laser fiber assembly as defined in claim 1 wherein the distal end of the jacket member is spaced approximately 0.5 to 12 millimeters from the bend in the optical fiber.

9. A side-firing laser fiber assembly as defined in claim 1 wherein the end of the jacket member is spaced approximately 2 to 8 millimeters back from the bend in the optical fiber.

10. A side-firing laser fiber assembly as defined in claim 1 wherein the distal end of the jacket member is spaced approximately 3.5 to 5.5 millimeters from the bend in the optical fiber.

11. A side-firing laser fiber assembly as defined in claim 1 wherein the distal end of the jacket member is spaced approximately 3.5 millimeters from the bend in the optical fiber.

12. A side-firing laser fiber assembly as defined in claim 1, 3, 4, 5, 6, 7, 9, 10 or 11 wherein the arcuate edge has a radius of approximately 0.15 to 0.30 millimeters.

13. A side-firing laser fiber assembly as defined in claim 1, 3, 4, 5, 6, 7, 9, 10 or 11 wherein the arcuate edge has a radius of approximately 0.19 millimeters.

14. A side-firing laser fiber assembly as defined in claim 1, wherein the optical fiber is formed from a material selected from the group consisting of quartz, silica and thermoplastic.

15. A side-firing laser fiber assembly for use in performing laser surgical procedures, comprising:
    an optical fiber having a diameter of approximately 1000 microns, said optical fiber having an input end and an output end;

the input end being adapted for connection to a laser source; and the output end terminating in a substantially flat face from which substantially all of the laser energy from said laser source is emitted;

said face having an arcuate edge having a radius of approximately 0.15 to 0.30 millimeters around the circumference of said face;

said output end having a bend formed proximally of said flat face so that laser energy emitted from said flat face is directed at a side-firing angle with respect to the longitudinal axis of the main body of the optical fiber; and a jacket member over most of the length of the optical fiber member.

16. A side-firing laser fiber assembly as defined in claim 16, wherein the arcuate edge has a radius of approximately 0.19 millimeters.

17. A side-firing laser fiber assembly as defined in claim 15, wherein the bend formed proximally of the flat face is at an angle of approximately 135 to 155 degrees with respect to the longitudinal axis of the main body of said optical fiber.

18. A side-firing laser fiber assembly as defined in claim 15, wherein the bend formed proximally of the flat face is at an angle of approximately 135 degrees with respect to the longitudinal axis of the main body of said optical fiber.

19. A side-firing laser fiber assembly as defined in claim 15, wherein the bend formed proximally of the flat face is at an angle of approximately 145 degrees with respect to the longitudinal axis of the main body of said optical fiber.

20. A side-firing laser fiber assembly as defined in claim 15 wherein the optical fiber is formed from a material selected from the group consisting of quartz, silica and thermoplastic.

21. A method for effecting deep tissue coagulation and necrosis comprising the steps of:

obtaining a laser fiber assembly as defined in claim 1;

situating the emitting end of said laser fiber assembly adjacent tissue in which it is desired to effect deep tissue coagulation and tissue necrosis; and directing laser energy upon said tissue in order to effect deep tissue coagulation and necrosis.

22. A method for effecting deep tissue coagulation and necrosis comprising the steps of:

obtaining a laser fiber assembly as defined in claim 15, 16, 17, 18 or 19;

situating the emitting end of said laser fiber assembly adjacent tissue in which it is desired to effect deep tissue coagulation and tissue necrosis; and directing laser energy upon said tissue in order to effect deep tissue coagulation and necrosis.

23. A method as defined in claim 21 for treating benign prostatis hyperplasia further comprising the steps of obtaining an endoscopic instrument suitable for insertion into the urethra of a patient suffering from benign prostatis hyperplasia; and inserting said endoscopic instrument into the urethra of a patient suffering from benign prostatis hyperplasia so as to direct the laser energy in the region of the patient's prostate where it is desired to effect deep tissue coagulation and necrosis.

24. A method for effecting deep tissue coagulation and necrosis comprising the steps of:

obtaining a laser fiber assembly including an optical fiber having an input end adapted for connection to a laser source; and an output end terminating in a substantially fiat face from which substantially all of the laser energy from said laser source is emitted, said face having an arcuate edge around the circumference thereof;

situating the emitting end of said laser fiber assembly adjacent tissue in which it is desired to effect deep tissue coagulation and tissue necrosis; and directing laser energy upon said tissue in order to effect deep tissue coagulation and necrosis.

25. A method as defined in claim 24, wherein the output end of the optical fiber is further provided with a bend formed proximal to said fiat face so that laser energy emitted from said fiat face is directed at a side-firing angle with respect to the longitudinal axis of the main body of the optical fiber.

26. A method as defined in claim 24, wherein the optical fiber has a diameter of approximately 1000 microns and wherein the arcuate edge of the flat face has a radius of approximately 0.15 to 0.30 millimeters around the circumference of said face.

27. A method as defined in claim 24, wherein the optical fiber has a diameter of approximately 1000 microns and wherein the arcuate edge has a radius of approximately 0.19 millimeters.

28. A method as defined in claim 25, wherein the bend formed proximal to the flat face is at an angle of approximately 135 to 155 degrees with respect to the longitudinal axis of the main body of the optical fiber.

29. A method as defined in claim 25, wherein the bend formed proximal to the flat face is at an angle of approximately 135 degrees with respect to the longitudinal axis of the main body of the optical fiber.

30. A method as defined in claim 25, wherein the bend formed proximal to the flat face is at an angle of approximately 145 degrees with respect to the longitudinal axis of the main body of the optical fiber.

31. A method for treating benign prostatis hyperplasia further comprising the steps of obtaining an endoscopic instrument suitable for insertion into the urethra of a patient suffering from benign prostatis hyperplasia;

obtaining a laser fiber assembly including an optical fiber having an input end adapted for connection to a laser source and an output end terminating in a substantially flat face from which substantially all of the laser energy from said laser source is emitted said face having an arcuate edge around the circumference thereof;

inserting said endoscopic instrument and said laser fiber assembly into the urethra of a patient suffering from benign prostatis hyperplasia; and directing laser energy to the region of the patient's prostate where it is desired to effect deep tissue coagulation and necrosis.

32. A method as defined in claim 31, wherein the output end of the optical fiber is further provided with a bend formed proximal to said fiat face so that laser energy emitted from said fiat face is directed at a side-firing angle with respect to the longitudinal axis of the main body of the optical fiber.

33. A method as defined in claim 31, wherein the optical fiber has a diameter of approximately 1000 microns and wherein the arcuate edge of the flat face has a radius of approximately 0.15 to 0.30 millimeters around the circumference of said face.

34. A method as defined in claim 31, wherein the optical fiber has a diameter of approximately 1000 microns and wherein the arcuate edge has a radius of approximately 0.19 millimeters.

35. A method as defined in claim 32, wherein the bend formed proximal to the flat face is at an angle of approximately 135 to 155 degrees with respect to the longitudinal axis of the main body of the optical fiber.

36. A method as defined in claim 32, wherein the bend formed proximal to the flat face is at an angle of approximately 135 degrees with respect to the longitudinal axis of the main body of the optical fiber.

37. A method as defined in claim 32, wherein the bend formed proximal to the flat face is at an angle of approximately 145 degrees with respect to the longitudinal axis of the main body of the optical fiber.

* * * * *

UNITED STATES PATENT AND TRADEMARK OFFICE
CERTIFICATE OF CORRECTION

PATENT NO. : 5,416,878
DATED : May 16, 1995
INVENTOR(S) : JOHNNY M. BRUCE

It is certified that error appears in the above-indentified patent and that said Letters Patent is hereby corrected as shown below:

Title page, column 2, item [57], Abstract, line 23, "prostatis hyperplasia" should be --prostatic hyperplasia--
Column 2, line 5, "an physician" should be --a physician--
Column 3, line 45, before "benign" insert --make it particularly useful in treatment of conditions such as--
Column 3, line 45, "prostatis hyperplasia" should be --prostatic hyperplasia--
Column 9, line 56, "prostatis hyperplasia" should be --prostatic hyperplasia--
Column 9, line 60, "prostatis hyperplasia" should be --prostatic hyperplasia--
Column 9, lines 62-63, "prostatis hyperplasia" should be --prostatic hyperplasia--
Column 10, line 4, "fiat face" should be --flat face--
Column 10, lines 16 and 17, "fiat face" should be --flat face--
Column 10, lines 41-42, "prostatis hyperplasia" should be --prostatic hyperplasia--
Column 10, line 45, "prostatis hyperplasia" should be --prostatic hyperplasia--
Column 10, line 50, after "emitted" insert --,--
Column 10, line 55, "prostatis hyperplasia" should be --prostatic hyperplasia--

UNITED STATES PATENT AND TRADEMARK OFFICE
CERTIFICATE OF CORRECTION

PATENT NO. : 5,416,878
DATED : May 16, 1995
INVENTOR(S) : Johnny M. Bruce

It is certified that error appears in the above-indentified patent and that said Letters Patent is hereby corrected as shown below:

Column 10, lines 61 and 62, "fiat face" should be --flat face--.

Signed and Sealed this

Tenth Day of October, 1995

Attest:

BRUCE LEHMAN

Attesting Officer

Commissioner of Patents and Trademarks